United States Patent [19]

Carsenti-Etesse et al.

[11] Patent Number: 5,498,416

[45] Date of Patent: Mar. 12, 1996

[54] PROCESS FOR THE PROTECTION OF PROSTHESES AND OF TEMPORARILY OR PERMANENTLY IMPLANTABLE MATERIAL AGAINST BACTERIAL COLONIZATION AND INFECTION

[76] Inventors: Helene J. Carsenti-Etesse; Pierre L. Dellamonica, both of 101 Chemin du Col de Bast, Nice, France, 06100

[21] Appl. No.: 182,090

[22] PCT Filed: Jul. 17, 1992

[86] PCT No.: PCT/FR92/00694

§ 371 Date: Jan. 18, 1994

§ 102(e) Date: Jan. 18, 1994

[87] PCT Pub. No.: WO93/01842

PCT Pub. Date: Feb. 4, 1993

[30] Foreign Application Priority Data

Jul. 18, 1991 [FR] France ................... 91 09069

[51] Int. Cl.⁶ .................. B05D 3/00; B05D 1/36; A61F 2/00; A61M 5/32
[52] U.S. Cl. .................. 424/422; 424/423; 604/265; 427/2.1; 427/2.24; 427/2.28; 427/2.3
[58] Field of Search .................. 427/2.1, 2.12, 427/2.28, 2.3, 2.31; 424/422, 423; 604/265

[56] References Cited

U.S. PATENT DOCUMENTS

| | | | |
|---|---|---|---|
| 3,695,921 | 10/1972 | Shepherd et al. | 427/2.28 |
| 3,877,951 | 4/1975 | Pojurowsky | 427/2.1 |
| 4,837,079 | 6/1989 | Quantrille et al. | 427/428 |
| 4,925,668 | 5/1990 | Khan et al. | 427/2.3 |
| 5,019,096 | 5/1991 | Fox, Jr. et al. | 427/2.3 |
| 5,023,107 | 6/1991 | Roberts | 427/2.27 |
| 5,089,205 | 2/1992 | Huang et al. | 427/2.3 |

FOREIGN PATENT DOCUMENTS

| | | |
|---|---|---|
| 0141628 | 5/1985 | European Pat. Off. . |
| 0207624 | 1/1987 | European Pat. Off. . |
| 0328421 | 8/1989 | European Pat. Off. . |
| 0379269 | 7/1990 | European Pat. Off. . |
| 2093348 | 9/1982 | United Kingdom . |
| WO89/04674 | 6/1989 | WIPO . |

*Primary Examiner*—Diana Dudash
*Attorney, Agent, or Firm*—Young & Thompson

[57] ABSTRACT

A method for protecting prostheses and temporarily or permanently implantable materials from bacterial colonization and infection, wherein the material is successively impregnated with: (a) a biguanide solution having the general formula (I)

$$R_1R_2N-\overset{NH}{\underset{\|}{C}}-NH-\overset{NH}{\underset{\|}{C}}-NH-(CH_2)_n-NH-\overset{NH}{\underset{\|}{C}}-NH-\overset{NH}{\underset{\|}{C}}-NR_1R_2$$

wherein $R_1$ is an alkyl, aminoalkyl, optionally substituted phenyl, naphthyl or cyano radical, $R_2$ is a hydrogen atom or an alkyl radical and n is an integer from 1–6, with the proviso that the alkyl radicals and portions are linear or branched and contain 1–4 carbon atoms; and (b) a solution of an antibacterial agent which may be gradually redistributed in an aqueous medium; whereafter the material thereby impregnated is dried.

9 Claims, No Drawings

PROCESS FOR THE PROTECTION OF PROSTHESES AND OF TEMPORARILY OR PERMANENTLY IMPLANTABLE MATERIAL AGAINST BACTERIAL COLONIZATION AND INFECTION

FIELD OF THE INVENTION

The present invention relates to a process for the protection of protheses, implants and/or catheters, of temporary or permanent implantable material, against bacterial colonization and infection, as well as equipment permitting obtaining this protection.

BACKGROUND OF THE INVENTION

The impregnation of catheters by quinolines has been described in numerous publications.

The publication EP-A-0 328 421 relates to a known method of antibacterial securement by a matrix of polymeric resin, first dissolved in an organic solvent. It is this resin which will then be secured on the polymer. This mode of securement is indirect.

The publication EP-A-0 207 624 relates to methods of preparation of an anti-infection polymer in a direct manner, comprising different stages. First, an immersion of the polymer in a solution of antimicrobial agents dissolved in an organic solvent, then, the immersion of the polymer in an organic solvent which can contain metallic salts, finally the immersion of the polymer in an organic solvent containing antimicrobials. It is dried after this immersion.

The publication EP-A-0 379 269 relates to the incorporation of chlorhexidine in a polymer during its manufacture. This technique uses a heating as well as a quaternary ammonium compound of the type of tridodecyl methyl ammonium chloride (TDMAC) so as to permit ultimate securement of the antibiotic. It is thus an indirect utilization. On the other hand, the doctor who wishes to use this type of technique must dip the polymer in the antimicrobial just before its use because there is no possibility of preserving the polymer treated with the antibiotic.

The publication EP-A-0 141 628 relates to the use of chlorhexidine and therefore of its cationic functions for the direct securement on latex. In this document, there is no question of securing an antimicrobial or an antibacterial.

The publication GB-A-2 093 348 uses, to secure the antimicrobial or the antibacterial, plaster of Paris.

Finally, the publication WO-A-8 904 674 relates to the securement of an antimicrobial on a biodegradable polymer.

SUMMARY OF THE INVENTION

Contrary to most of these publications, the present invention uses first a biguanide which will be secured on a polymer such as a catheter, a prothesis or a suture strand, so as to permit thereafter, and only thereafter, the securement of the antimicrobial. This successive effect is not taught in any of the above-mentioned publications.

On the other hand, this sequence permits not having to use either a solvent or a resin and thus afterward to have a much more simple operation which permits the conservation of the medical objects which have been treated and the sterilization by ethylene oxide, which assures ease of use for the surgeon who will have at his disposal a sterile material ready to use.

The adhesion of these antibacterial agents on the medical materials being difficult, there is as a result a protection insufficient to avoid consecutive bacterial infections upon use of the prothesis.

The impregnation of catheters by biguanides is also described in Japanese patent application 60-036064. These protections are nevertheless insufficient and can give rise to toxicological problems upon leaching out of the biguanides.

Despite the researches undertaken, the cases of infection in the presence of foreign material are greatly increasing.

Infections brought on by the implantation of protheses can be particularly of endocardital origin and require difficult treatments which may even be impossible. The failure of these treatments leads most often to the loss of material; there is a high social cost and a substantial risk for the patient.

The present invention permits overcoming the problems of securement and toxicity of the antibacterial substance, and thus gives rise to improved efficacy.

DETAILED DESCRIPTION OF THE INVENTION

There has been discovered a protective process according to which the prothesis is successively impregnated, which is not proposed by the publications mentioned above:

1) by a solution of biguanide of the general formula:

$$R_1R_2N-C-NH-C-NH-(CH_2)_n-NH-C-NH-C-NR_1R_2$$

in which $R_1$ represents an alkyl radical, aminoalkyl, phenyl possibly substituted (by a halogen atom or a hydroxy, alkyl, alkoxy or carboxy radical), naphthyl or cyano, $R_2$ represents a hydrogen atom or an alkyl radical and n represents a whole number from 1 to 6, wherein the alkyl radicals and portions mentioned above are straight or branched and contain 1 to 4 carbon atoms, then 2) by a solution of an antibacterial agent capable of being redistributed progressively in aqueous medium, then the prothesis thus impregnated is dried.

The suitable antibacterial agents are selected from the class of quinoline, β-lactams, fusidic acid, phosphomycine, teicoplanine, aztreoname or imipeneme.

The process according to the invention permits not only protecting against bacterial proliferation, but moreover, by using the biguanide as adhesion agent, permits solving the double problem of poor adhesion of the quinolines and other antibiotics to prostheses, implants and catheters and the toxicity of the biguanides when they serve themselves as antibacterial substance.

To achieve this result, there are used the cationic functions carried by the hydrogenated amine functions of the biguanide and the anionical functions carried by the antibiotics; said cationic and anionic functions comprise an ionic bond permitting the fixation of the antibiotics to the biguanide.

This process has the advantage of being able to be applied to any sort of prothesis utilizable in medicine and of assuring a diffusion of the antibiotic directly from the implanted material.

By way of example, the catheters, implants and protheses can be selected from urinary catheters, probes, vascular and intraarterial catheters, cardiacal valvular protheses, arterial protheses, cardiac simulators, orthopedic protheses, ocular or dental implants, shunts that are connecting two segments of the circulatory system, as well as suture thread.

The process according to the invention is applicable to various materials such as plastics, metals or suture threads.

The biguanide solutions employed are preferably selected from aqueous or organic solutions and solvents such as alcohols (for example ethanol, methanol) polypropyleneglycol, polyethyleneglycols or glycerol.

Without limitation, the preferred biguanides are chlorhexidine: hexamethylene bis [(p-chlorophenol)-5 biguanide] -1, 1', alexidine: hexamethylene bis [(ethyl-2 hexyl')-5 biguanide]-1, 1', or hexamethylene bis [aminohexylbiguanide]-1, 1'.

The solutions containing the antibiotic will be adapted to the nature and class of the antibiotic chosen. By way of example, in the case of the quinolines, solutions in alcohol (ethanol for example) or in chlorinated solvents will be particularly adapted in the case of the β-lactams, for use more especially of the following solvents: distilled water, ethanol, methanol.

By way of example, among the classes of antibiotics cited above, the products hereinafter are particularly preferred: pefloxacine, norfloxacine, sparfloxacine, enoxacine, ciprofloxacine, ofloxacine, fleroxacine, lomefloxacine, temafloxacine, amoxacillin, oxacillin, ceftriaone, cefsulodine, ceftazidime.

The effectiveness of the device according to the invention has been demonstrated on the following conditions:

MATERIAL AND METHOD

STUDY OF MODALITIES OF FIXATION OF THE ANTIBIOTIC antibiotic to vary. The coated catheters are tested to determine their residual activity with chlorhexidine, to study the concentration of fixed antibiotic, to study the stability and operation with time of this coating.

"COATING" MODALITIES a) Fixation on microtitration plates:

The plates are incubated one night at ambient temperature in the presence of chlorhexidine at a variable concentration (Table I, columns 2 to 11). The plates are then rinsed in water that is distilled or not and dried. The antibiotic is then distributed in the small cups of column 7 to column 11 (Table II). Incubation is then carried out overnight. The plates are then emptied, oven dried and stored at ambient temperature, covered to avoid any contamination by environmental bacteria. They are used after a minimum time of 8 to 60 days after coating, so as to ensure the stability of the fixation of the antibiotic.

This delay until use facilitates the operations of the surgeons who do not need, as with the techniques previously used, to immerse the microtitration plates or other supports in an antibiotic agent just before their use.

TABLE I

|   | 1 | 2 | 3 | 4 | 5 | 6 | 7 | 8 | 9 | 10 | 11 | 12 |
|---|---|---|---|---|---|---|---|---|---|----|----|----|
| A |   | CH | CH | CH | CH | CH | CH | CH | CH | CH | CH |   |
| B |   | CH | CH | CH | CH | CH | CH | CH | CH | CH | CH |   |
| C |   | CH | CH | CH | CH | CH | CH | CH | CH | CH | CH |   |
| D |   | CH | CH | CH | CH | CH | CH | CH | CH | CH | CH |   |
| E |   |   |   |   |   |   |   |   |   |    |    |   |
| F |   |   |   |   |   |   |   |   |   |    |    |   |
| G |   |   |   |   |   |   |   |   |   |    |    |   |
| H |   |   |   |   |   |   |   |   |   |    |    |   |

CH: chlorhexidine
P: Pefloxacine

TABLE II

|   | 1 | 2 | 3 | 4 | 5 | 6 | 7 | 8 | 9 | 10 | 11 | 12 |
|---|---|---|---|---|---|---|---|---|---|----|----|----|
| A |   | CH | CH | CH | CH | CH | CH + P | CH + P | CH + P | CH + P | CH + P |   |
| B |   | CH | CH | CH | CH | CH | CH + P | CH + P | CH + P | CH + P | CH + P |   |
| C |   | CH | CH | CH | CH | CH | CH + P | CH + P | CH + P | CH + P | CH + P |   |
| D |   | CH | CH | CH | CH | CH | CH + P | CH + P | CH + P | CH + P | CH + P |   |
| E |   |   |   |   |   |   |   |   |   |    |    |   |
| F |   |   |   |   |   |   |   |   |   |    |    |   |

CH: chlorhexidine
P: Pefloxacine on microplates of polyvinyl (NUNC) and polystyrene (DYNATECH)
on polyurethane catheters.

The concentration of the biguanides necessary as well as the nature of the solvent is studied (distilled water, ethyl alcohol, methyl alcohol).

On microplates, a study of feasibility has been carried out, then a study of the consequences of the fixation of the antibiotic on the property of adhesion of different germs.

On catheters, a study of feasibility has been carried out with modalities of fixation causing the concentrations of The effectiveness of the fixation of the antibiotic is carried out with a view toward the antibiotic and antiadherent properties of the antibiotic fixed on the small cups relative to the germs which are sensitive and/or resistant thereto. The method used for the study of the properties of adherence is that described by CHRISTENSEN G. D. et al., *J. Clin. Microbiol.*, 22, 996–1006 (1985). A bacterial suspension (inoculation of $10^6$ UFC/ml obtained by dilution of a culture overnight) is distributed in the small cups of the microplate to be tested.

After a period of incubation of six hours at an oven temperature of 37° C., the small cups are emptied, rinsed three times with phosphate buffer pH=7 then the remaining adherent bacteria are fixed with alcohol and rendered visible by coloration with crystalline violet. A reading of the optical densities (OD) is effected by spectrometry (540 nm).

The results of the small cups with the fixed antibiotic are expressed in percentage of adhesion relative to a standard (clean small cups) and relative to small cups with chlorhexidine alone. Each experiment is carried out on the same plate in at least four small cups and on three different plates.

The results are expressed by the mean of the percentages of adherence and a statistical study is effected by the test t of STUDENT.

b) Fixation on catheters: In vitro studies

The modalities of fixation of the antibiotic are studied by causing to vary: the concentrations of chlorhexidine and the concentrations of antibiotics.

A study of stability of the catheters as a function of time is effected by a measurement of the antibiotic activity of the catheters stored for two months. The antibiotic activity is determined in vitro by the method of KIRBY-BAUER. The portions of catheters are implanted vertically in a gelose inoculated by inundation with a selected germ (*Staphylococcus aureus, Escherichia coli, Micrococcus lutea, Enterobacter cloacae, Serratia marcescens* . . . ) After inoculation, overnight at 37° C., the inhibition diameters are measured, compared to those of the uncoated catheters and standard chlorhexidine catheters.

It has thus been demonstrated by causing to vary the antibiotic concentrations (for example the pefloxacine), that the fixation is dose dependent.

STUDY OF RELEASE OF THE ANTIBIOTIC

Extraction of the antibiotic in a buffered solution which is renewed to determine the liberation of the antibiotic in case of liquid renewal.

In vivo study

Pieces of catheters coated with pefloxacine are implanted intraperitonealy according to an infection model on a catheter. After emplacement of the catheters, the infection is provoked by injection of an inoculum of *Staphylococcus aureus* variable according to experiments. This inoculum is injected either 24 hours after emplacement of the catheters, or just after this implantation. After 24 and 48 hours, the mice are sacrificed, the catheters are removed, treated by sonication, trypsin to loosen the adherent bacteria and cultivated on gelose to enumerate their bacterial contamination. Concomitant removals are effected: liver, spleen and blood.

These experiments are carried out relative to standard groups of mice in which are implanted catheters to which antibiotic is not fixed.

In the elution liquids of the catheters, are provided the present antibiotic dosages as well as the removed catheters; the residual antibiotic is dosed by direct implantation of the catheter in the gelose.

c) Study of fixation on metallic implants:

Pieces of metal (steel or titanium alloy constituting examples of materials used for metallic prostheses) are fixed with pefloxacine under the same conditions, then tested by implantation of the specimens in the gelose.

d) Studies of the fixation on suture filaments:

After fixation according to the same procedures, the dried filaments stored for 15 days to two months are tested for their antibiotic activity on geloses seeded with various germs and this relative to uncoated control filaments or having fixed thereon only chlorhexidine.

RESULTS

I—RESULTS WITH MICROTITRATION PLATES

Fixation of pefloxacine

The plates are first incubated overnight at ambient temperature with chlorhexidine (CH) at concentrations of 0.2%, 1%, 2% and 10% in distilled water, ethyl alcohol and methyl alcohol. Certain ones are washed and dried, others simply washed before distribution on the portion of the plate of pefloxacine with variable concentration.

The results showed the influence of washing the plates after the time of fixation of CH and before the antibiotic, on the antiadherent activity relative to the acinetobacter, showing that the fixation is more efficacious if washing is not effected before impregnation with the antibiotic. Variable concentrations of chlorhexidine are studied. The results of the antiadherent activity of the pefloxacine, on sensitive germs and resistant germs, show the greatest activity is obtained with a chlorhexidine concentration of 10%.

II—EXUDATION OF THE PEFLOXACINE FIXED ON THE CATHETER

The catheter impregnated with a solution containing 10% of chlorhexidine and with a solution of 2 g/l of pefloxacine is placed in 1 ml of buffer. The concentration of pefloxacine in the buffer is measured after 1 and 24 hours of incubation at 37° C.: 2.4 and 2.6 mg/l respectively. The initial buffer is removed and then a dosage is effected after incubation at 37° C. overnight. The residual weight is then 0.3 mg/l. This experiment permits showing that it is possible to let the antibiotic diffuse into the medium from the catheter. This diffusion is effective from 1 to 24 hours.

III—IN VIVO STUDY

The results show that if the bacterial inoculum is injected 24 hours after emplacement of the coated catheters, no significant protection is obtained. In contrast, if the inoculum is injected the same day as the emplacement of the catheters (which corresponds to the infection model in human surgery), a significant difference is observed on the logarithmic media UFC/ml on catheters with an inoculum of $10^6$ UFC/ml. This difference is more significant if the catheters are removed after 48 hours. Similarly, with bacterial inoculum of $10^5$ UFC/ml, if the protection provided by the coated catheters is insignificant after 24 hours, it is significant after 48 hours. With infected pefloxacine catheters, the bacterial colonization is also significantly diminished relative to contaminated control catheters.

IV—STUDY ON METALLIC IMPLANTS

Under the conditions previously described, a fixation of the pefloxacine is obtained after treatment by immersion in a 10% chlorhexidine solution of titanium alloys and fragments of stainless steel.

The results show an increase of the diameter of inhibition relative to a nonimpregnated standard, for all the germs studied.

Generally speaking, the protection process according to the invention is practiced by immersing the prothesis, the implant or the catheter in a solution containing 20 to 100 g/l of biguanide, as the case may be washing, immersing in a solution containing 1 to 100 g/l of antibiotic, then as the case may be washing and drying.

The duration of immersion is not a necessary factor for the practice of the invention. However, it is preferable to effect immersion for 1 to 24 hours in each of the solutions.

The protheses and/or the catheters impregnated according to the process of the present invention are adapted to release progressively the antibacterial substances into the implantation medium for at least 24 to 48 hours, and thus to provide prevention of bacterial contamination of the materials utilized.

The present invention relates also to the device for the protection of protheses, implants and/or catheters obtained according to the process previously described and adapted to release progressively the antibacterial substance fixed on the surface.

The use for this device is substantial because of its effectiveness and its absence of toxicity as the biguanide is not or is only very little released into the implantation medium.

According to the present invention, the impregnation of protheses, implants and/or catheters can be effected without regard to what precedes, for example consecutively to manufacture of the process or at the moment of use.

The present invention also relates to equipment permitting easily proceeding with the implantation of the catheter, the implant or the prothesis.

Such equipment is constituted:

a) by a solution containing 20 to 100 g/l of biguanide of the general formula (I) for example designated solution No. 1 and adapted for the first impregnation and b) by a solution containing 1 to 100 g/l of the antimicrobial substance for example designated solution No. 2 and adapted for the second impregnation.

The practice of the process according to the invention is thus facilitated in the case in which the protheses and/or catheters are supplied without a device for antibacterial protection.

Alternatively, for example in the case of substances which can give rise to problems of stability and solution over a long period of time, it is of course possible that such equipment can also include, in place of the vial of solution ready to use, a vial of solvent and the appropriate quantity of the substance which will be dissolved at that time by the user at the time of its use.

The impregnation with the biguanide solution can also be carried out immediately following production of the material to be implanted, the second impregnation being adapted to be performed at the time of use, for example in the case of a relatively unstable antibiotic.

We claim:

1. In a process for the protection of prostheses, implants and/or catheters, of temporary or permanent implantable materials, against bacterial colonization and infection in which there is applied to a material to be protected, a solution of an antibacterial agent capable of being progressively released into aqueous medium, the improvement which comprises: successively impregnating said material to ensure the adhesion of the antibacterial agent to the material to be protected:

a) with a solution in aqueous or organic solvent of a biguanide of the general formula:

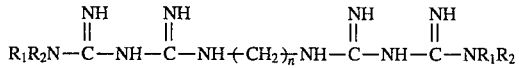

in which $R_1$ represents an alkyl radical, aminoalkyl, phenyl possibly substituted (with a halogen atom or a hydroxy, alkyl, alkoxy or carboxy radical), naphthyl or cyano, $R_2$ represents a hydrogen atom or an alkyl radical and n is a whole number from 1 to 6, wherein the alkyl portions and radicals are a straight chain or branched and contain 1 to 4 carbon atoms, then b) with the solution of antibacterial agent capable of being progressively released into aqueous medium, and drying the thus-impregnated material.

2. Process according to claim 1, wherein the material to be protected is dried between impregnation with the biguanide solution and impregnation with the solution of antibacterial agent.

3. Process according to claim 1, wherein the material to be protected, after impregnation with the biguanide solution, is not washed prior to impregnation with the antibacterial agent solution.

4. Process according to claim 1, wherein the biguanide is chlorhexidine, alexidine or hexamethylene bis [aminohexyl biguanide] -1, 1'.

5. Process according to claim 1, wherein the antibacterial agent is selected from the group consisting of quinolines, β-lactams, fusidic acid, phosphomycine, teicoplanine, aztreoname and imipeneme.

6. Process according to claim 1, wherein the antibacterial agent is pefloxacine.

7. Process according to claim 1, wherein the biguanide solution contains 20 to 100 g/l of biguanide.

8. Process according to claim 1, wherein the solution of antibacterial agent contains 1 to 100 g/l of antibacterial agent.

9. An infection-resistant device capable of progressively releasing in aqueous medium an amount of an antibacterial substance fixed to the device, said amount being effective to prevent bacterial contamination of the device, said device comprising a first coating from a solution in aqueous or organic solvent of a biguanide of the general formula:

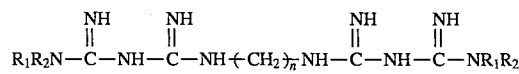

in which $R_1$ represents an alkyl radical, aminoalkyl, phenyl possibly substituted (with a halogen atom or a hydroxy, alkyl, alkoxy or carboxy radical), naphthyl or cyano, $R_2$ represents a hydrogen atom or an alkyl radical and n is a whole number from 1 to 6, wherein the alkyl portions and radicals are a straight chain or branched and contain 1 to 4 carbon atoms, and a second coating from a solution of the antibacterial substance, said second coating overlying said first coating, and said first coating ensuring adhesion of the antibacterial substance to the device.

* * * * *